United States Patent [19]

Flynn

[11] Patent Number: 4,622,964

[45] Date of Patent: Nov. 18, 1986

[54] VALVE FOR BREATHING DEVICE

[75] Inventor: Stephen D. Flynn, Oakville, Canada

[73] Assignee: O-Two Systems International Inc., Mississauga, Canada

[21] Appl. No.: 708,544

[22] Filed: Mar. 5, 1985

Related U.S. Application Data

[63] Continuation-in-part of Ser. No. 536,539, Sep. 28, 1983, abandoned.

[51] Int. Cl.⁴ .................................................. A62B 7/04
[52] U.S. Cl. ................................. 128/205.24; 137/102; 137/908; 137/512.4
[58] Field of Search ........................ 128/205.24, 204.25, 128/205.13, 205.15, 205.17, 205.18, 207.12, 207.13, 207.16; 137/102, DIG. 9, 512.4

[56] References Cited

U.S. PATENT DOCUMENTS

| | | | |
|---|---|---|---|
| 2,954,793 | 10/1960 | Seeler | 137/102 |
| 3,425,409 | 2/1969 | Isaacson et al. | 128/205.18 |
| 3,435,839 | 4/1969 | Edder | 137/102 |
| 3,556,122 | 1/1971 | Laerdal | 137/102 |
| 3,978,878 | 9/1976 | Rudolph | 137/102 |
| 3,993,059 | 11/1976 | Sjostrand | 128/205.24 |
| 4,192,301 | 3/1980 | Hardwick | 128/205.24 |
| 4,267,832 | 5/1981 | Hakkinen | 128/205.24 |

FOREIGN PATENT DOCUMENTS 748363  5/1956  United Kingdom ............... 137/102

Primary Examiner—Henry J. Recla
Attorney, Agent, or Firm—George A. Rolston

[57] ABSTRACT

A breathing valve having a valve chamber connectable to a gas supply and to a breathing device, a gas flow opening for exit of exhaled gases through which atmospheric air may be inducted into the chamber, a valve member in the chamber, a one-way flow opening in the valve member through which gas may flow from the chamber for breathing, and preventing return flow in the opposite direction, a movable valve closure forming part of the valve member movable into and out of sealing engagement with the exit gas flow opening, and a pressure responsive device in the valve member responsive to obstruction of gas flow into the chamber and further responsive to inspiratory effort by a patient to cause the valve member to move away from the exit gas flow opening for permitting air flow through the exit gas flow opening into the chamber for inhalation.

8 Claims, 5 Drawing Figures

VALVE FOR BREATHING DEVICE

The invention relates to a two-way breathing valve for use in association with breathing equipment, such as equipment for the admistration of gases during resuscitation and the like. This application is a "Continuation-In-Part" of application Ser. No. 06/536,539 filed Sept. 28, 1983 entitled "Valve for Breathing Device" and now abandoned.

BACKGROUND OF THE INVENTION

When gases are administered, through a face mask, a valve is used which allows gas flow to take place through the mask into the patient's lungs, and when the patient exhales, the valve reverses and exhaled gas flows out to atmosphere. The patient may be unable to breath at all, or may be breathing spontaneously but with difficulty. The valve must therefore be capable of permitting spontaneous breathing, and also capable of permitting an assistant to carry out resuscitation.

One form of such a valve is shown in U.S. Pat. No. 4,071,025.

Equipment of this type is frequently used by paramedical personnel, nursing assistants, first aid workers, firemen, and service personnel. Such equipment is frequently required in an emergency, and in situations where malfunction of the equipment can occur for various reasons. For example, the gas supply can become blocked, due to a bend in a gas supply pipe for example. Similarly, a person being resuscitated is likely to vomit, and the vomit will enter the mask and may enter the valve itself.

Numerous other emergencies can also occur.

In many of these situations the result is that the valve becomes blocked, or gas flow from the gas supply into the valve is cut off.

In these situations, the assistant administering the gas may be distracted, and may not notice what has occurred. The patient is then in danger of suffocating.

Accordingly, it is desirable to provide in such a valve a means whereby in the event of a breakdown in the gas supply for any reason, atmospheric air is admitted to the valve, so that the patient can continue breathing.

Usually, the blocked valve or blocked gas supply condition will last only a few seconds at most, depending upon the experience of the assistant administering the gas. Once the assistant notices the problem, the mask is then quickly removed and either the valve must be dismantled and washed out, or the blockage in the supply must be cleared, and the valve and mask are then reassembled to continue treatment.

Again, these functions are done in an emergency situation, in many cases by persons who are not completely familiar with the way in which the equipment is designed.

When such valves are dismantled, the reassembly of the valve, if it involves many parts, may present serious problems. These problems will of course be greatly aggravated by the urgency of the situation. For all of these reasons therefore the design and fabrication of such valves becomes of critical importance to the success of the treatment. It is thus essential that the valve should be capable of providing the functions of gas inhalation, exhalation, and atmospheric air inhalation in the event of failure.

It is also essential that the valve shall have a minimum number of separate components, and that it may readily be disassembled, cleaned and reassembled by untrained personnel who are not familiar with the equipment. The valve must also be made of parts which are so arranged that it is impossible for the assistant to reassemble them in the wrong manner.

A somewhat improved form of valve is shown in Canadian Letters Patent No. 798,660. The valve shown in that patent involves two separate flexible valve members. One valve member opens to permit inhalation of gases, while the other valve member closes against the introduction of atmospheric air. On exhalation, the inlet valve moves away, and the exhalation valve opens up, allowing exhaled air to escape to atmosphere.

This type of valve is of a much simpler construction than that shown in earlier patents. However, it still does not provide for inhalation of atmospheric air in the event of a breakdown in the supply of gas. Consequently, although this form of valve can be cleaned and put back into service more easily than earlier forms of valve, in the event that it becomes clogged or blocked, it does not provide for the situation where the assistant who is administering the gas fails to notice that the gas supply has been cut off.

If in fact this should occur, and the gas supply becomes blocked for some reason, the patient will be unable to inhale atmospheric air, and will essentially suffocate quickly unless the mask is immediately removed.

Throughout this description, reference is made to the administering of a gas to a patient. It will of course be appreciated that the gas may be either pure oxygen, or air enriched with oxygen or ambient air, or a specially formulated mixture of gases.

In many circumstances where for example resuscitation is carried out in an emergency, special gases and oxygen supplies will not be available. In these cases, resuscitation is carried out simply by administering air by means of a manually operable bag. Numerous examples of such bags are shown in the prior art. One form of such bag is shown in U.S. Pat. No. 3,363,833. This form of bag is suitable for administering air alone, and may also be connected to a gas supply, so that it can be used for administering a gas.

For the purposes of this discussion therefore when reference is made to the administration of a gas, the term "gas" includes any mixture which may be breathed, including fresh air, oxygen, oxygen enriched air and specially formulated mixtures.

BRIEF SUMMARY OF THE INVENTION

With a view to overcoming these problems, the invention therefore comprises a breathing valve for use in association with breathing devices for the administration of a gas, and having a valve chamber having an upstream end, connectable to a supply of gas, and having a downstream end connectable to a breathing device, there being respective upstream and downstream opening means in said chamber communicating with respective said connection means, whereby gas can be admitted through said upstream opening, and can be administered through said downstream opening, said chamber means being of two-part construction, and including releaseable connection means whereby the same may be dismantled and reassembled, air flow opening means adjacent said downstream end, whereby exhaled air and gases may be discharged to atmosphere, and through which atmospheric air may be inducted into said chamber, a one-piece integral flexible valve member releaseably fastened in said chamber, one-way flow opening means in said valve member, whereby gas may flow from said chamber into said downstream opening, said valve member preventing return flow in the opposite direction, and said valve member further incorporating movable valve closure means movable into and out of sealing engagement with said air flow opening means in said downstream and of said chamber, whereby said seating means will close said openings, upon inhalation of gas from said upstream end of said chamber, and said seating means unsealing said air flow opening means upon exhalation, and means incorporated in said valve member normally holding said valve seating member away from said air flow openings, whereby upon the obstruction of gas flow into said chamber from said upstream end, air may flow through said air flow openings into said chamber for inhalation through said downstream end.

In this way a one-piece integral valve member is provided which provides all three functions, namely inhalation of gas, exhalation of exhaled air and gas, and inhalation of atmospheric air in the event of blockage of gas.

More particularly, the invention provides such a breathing valve in which such valve member incorporates a relatively rigid annular ring portion formed integrally therewith, for controlling the operation thereof.

A further and related objective of the invention is to provide the valve member with interference means which can be fitted in the chamber in only one position, to prevent assembly the wrong way around.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described preferred embodiments of the invention.

IN THE DRAWINGS

DESCRIPTION OF A SPECIFIC EMBODIMENT

Figure 1:
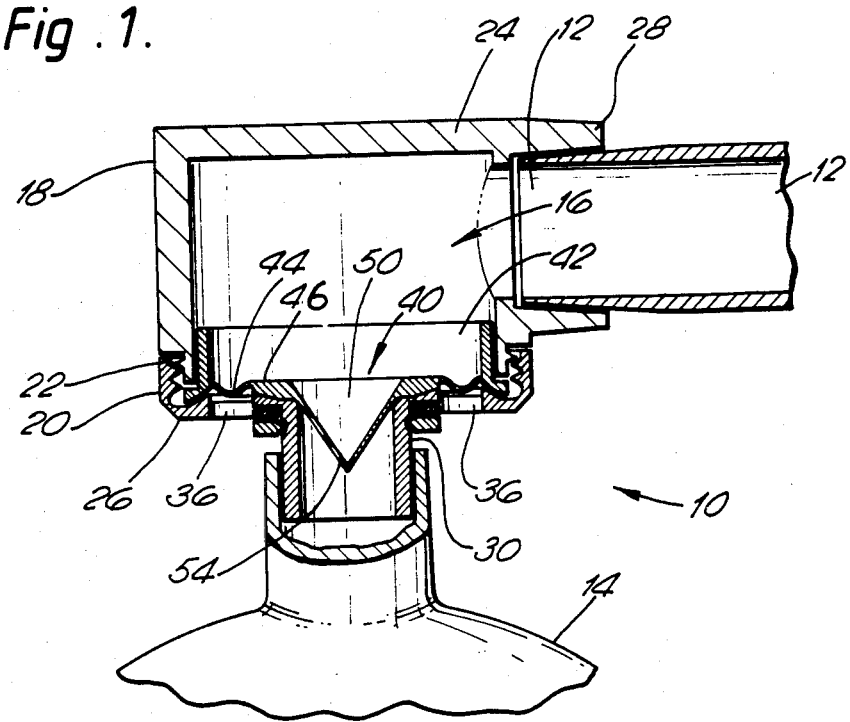
FIG. 1 is an elevational view of a typical gas administration system (without showing the bag or gas supply), and showing the valve according to the invention in section.

Referring now to FIG. 1, a valve according to the invention is shown generally as 10. For the sake of explanation only, it is shown connected to a gas supply pipe 12, at its upstream end, and at its downstream end, it is shown connected to a typical breathing mask 14.

It will of course be appreciated that the gas supply 12 is merely exemplary of a variety of different forms of supply that may be used. Thus such supply can come direct from gas supply cylinders, usually through a suitable pressure-reducing valve or metering device (not shown), the details of which are well known in the art and are omitted for the sake of clarity. Alternatively, the gas supply could simply be atmospheric air, supplied by means such as a air bag, such as that shown in the art, the details of which are omitted for the sake of clarity.

Similarly, the mask 14 could be any one of a wide variety of different masks, or other devices by means of which air or gas may be administered to a patient. Thus, for example, the mask 14 could be replaced by a breathing tube which is inserted down the windpipe, in the case of a person who requires special assistance.

It will also be well understood that the valve 10 according to the invention may be used in a wide variety of different circumstances, both in the operating theatre, ambulance, and in emergencies in the field, such as mines, hydroelectric service crews, swimming pools, fire locations and the like, and is intended for use by unskilled or only partly skilled assistants in all such locations.

For these reasons the valve 10 will be seen to comprise a chamber indicated generally as 16, which is in fact a two-part structure being formed of an upper generally cylindrical wall 18, and a lower generally cylindrical wall 20. Threaded means 22 are provided for fastening the two walls 18 and 20 together.

An upstream end wall 24 closes off the upper end of the cylindrical portion 18, and a downstream end wall 26 closes off the downstream end of the lower cylindrical wall 20.

A friction fit upstream connection sleeve 28 provides a means of coupling with the gas supply pipe 12. A downstream connector 30 having a retaining flange 32 is rotatably received in a central opening in wall 26. A snap-ring 34 secures connector 30 in position. Connector 30 is of a standard diameter to connect with other breathing devices.

Friction fit couplings of the type shown are generally standardised in the industry, and assist in preventing assembly in an incorrect manner.

However, it will be appreciated that other forms of connection may be provided in various different circumstances without substantially altering or modifying the design of the invention.

It will also be noted that flange 32 has a raised sealing ridge 35, for reasons described below.

The downstream end wall 26 is provided with a plurality of air flow openings 36, for the purpose of discharging exhaled air and gas, and also for the purpose of admitting fresh air in an emergency blockage situation.

The walls of valve chamber 16 are generally formed of clear plastic materials so that the interior of the chamber is readily visible. A releaseable locking device (not shown) can be provided for threads 22 if desired.

Within the valve chamber 16, there is provided the one-piece integral valve member or element indicated by the general reference 40. The valve member 40 will be seen to comprise a generally annular outer skirt portion 42 which is dimensioned to make a sliding fit within the interior of the upper cylindrical wall 18. Skirt 42 assists in locating the valve member centrally in the chamber, and also prevents assembly of the valve member in any orientation other than the correct one as shown.

A peripheral retaining flange 43 extends outwardly past the lowermost portion of wall 18, to retain valve member 40 in position.

An annular flexible web 44 extends inwardly from the skirt 42. Web 44 is dimensioned and oriented to overlay the air flow openings 36, and is thin and flexible for reasons described below.

Web 44 is formed into a generally annular concave fold as shown for reasons to be described. Located inwardly of web 44, is a somewhat more rigid annular seating ring 46, which is dimensioned to seat on sealing ridge 35 of flange 32. Ring 46 is relatively thick in relation to web 44. A tubular member 50 extends from the inner extremity of ring 46, and is designed to extend down the interior of connection portion 30. The tubular member 50 is essentially a pair of inwardly tapered flexible lips 52. Lips 52 meet one another at a slit 54, which is normally closed by the inherent inward bias of lips 52.

Ring 46 acts to isolate web 44 from tubular member 50. In this way, web 44 can flex, as described below, and ring 46 with member 50 will then move as a single unit.

It will be appreciated that valve member 40 is of integral one-piece construction, being formed of flexible resilient material such as synthetic rubber materials, typically silicone based plastic materials.

It is preferably of a bright distinctive colour to render it readily visible, so that its action can be observed when in use.

In operation, the valve structure 10 is usually interposed between a valve gas supply pipe 12 and a mask 14 or breathing device, as shown in FIG. 1, and the mask is placed over the face of the patient.

Gas is normally supplied under a slight positive pressure, eg., about 2 mm of mercury, through pipe 12, and will fill chamber 16. Flow of gas through the chamber 16 is however impeded or checked by the valve member 40. The inherent bias of lips 52 is sufficiently strong to overcome the slight gas pressure at this stage.

The patient may be unable to breathe, or may be breathing spontaneously. Where the patient is unable to breathe, then positive pressure is applied, typically by hand pressure on a compressible bag (not shown). The increased pressure in chamber 16 will then cause lips 52 to open and force gas or air into the lungs of the patient.

Where the patient is breathing spontaneously, the patient inhales and a slight negative pressure will then be developed in the mask 14.

Figure 2:
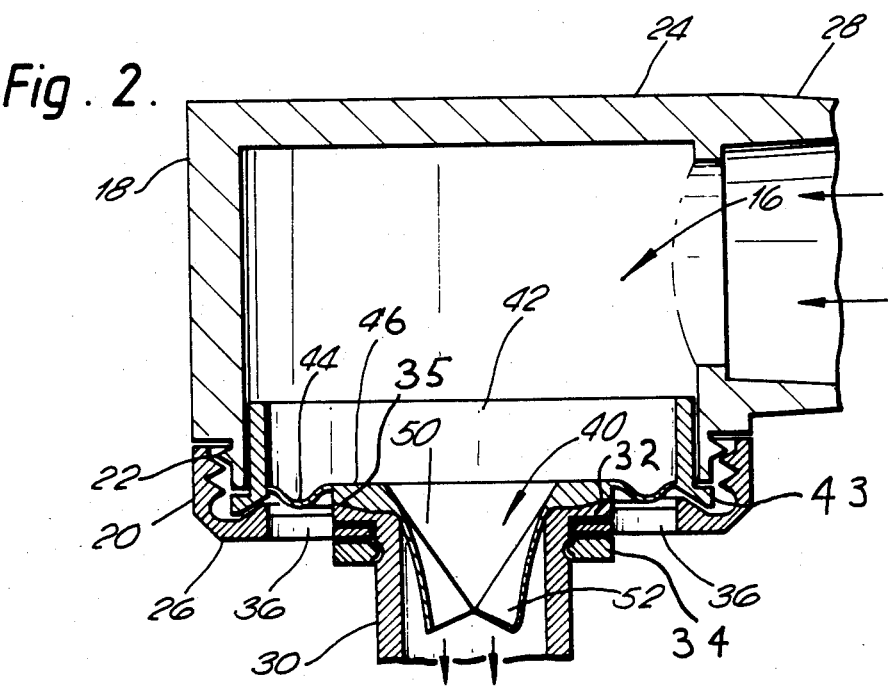
FIG. 2 is a greatly enlarged sectional view of the valve shown in FIG. 1, shown in the normal gas inhalation position.
Figure 3:
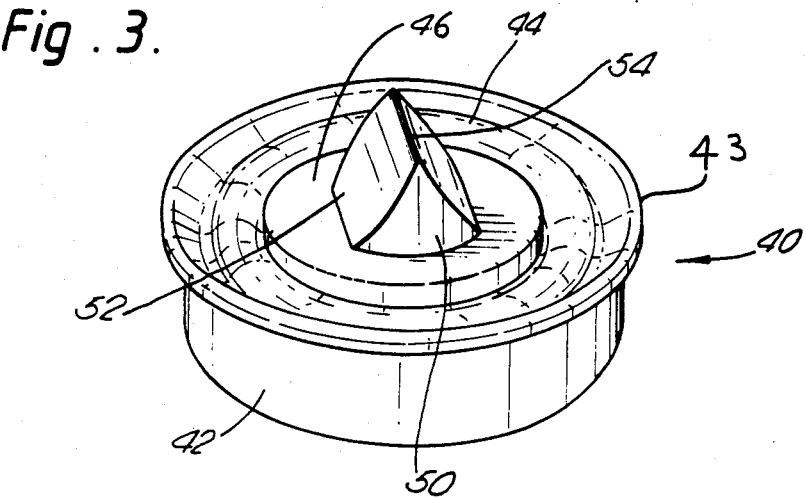
FIG. 3 is a perspective of the valve member.

This will then increase the pressure differential across the valve member 40. The inherent bias of lips 52 will then yield to the greater pressure differential, allowing gas to flow through the slit opening 54 as shown in FIG. 2.

Figure 4:
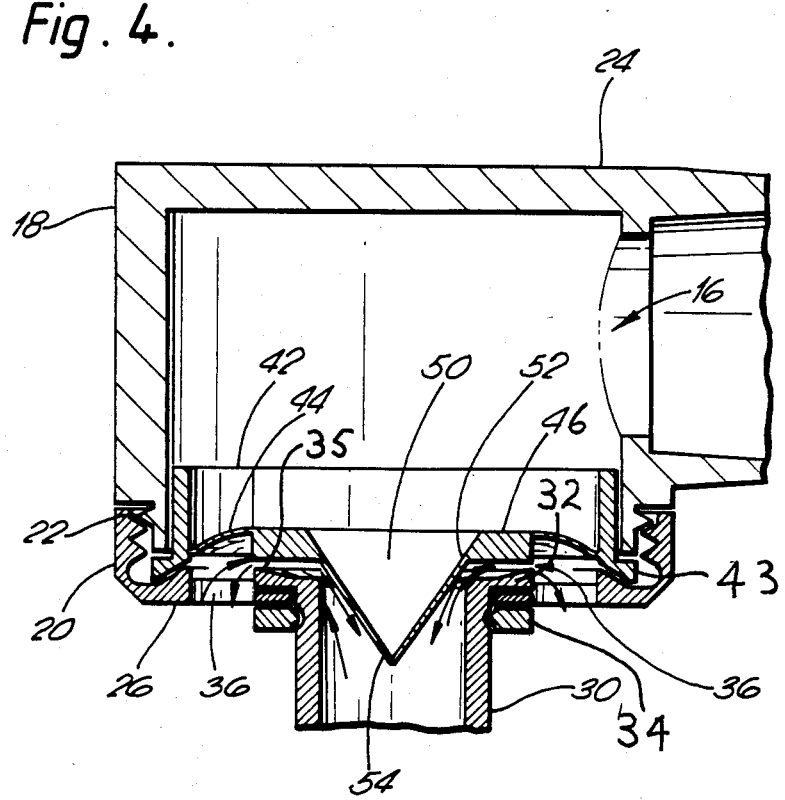
FIG. 4 is a sectional illustration corresponding to FIG. 2, and showing either exhalation or intake of fresh air, and, FIG. 5 is a section of an alternate embodiment.
Figure 5:
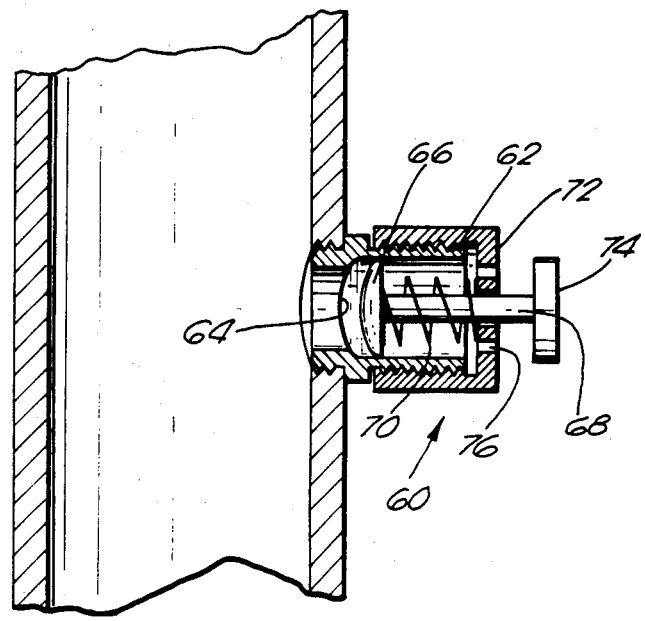

As the patient then exhales either consciously or unconsciously, a slight positive pressure is created in mask 14. This positive pressure will then cause valve member 40 to flex slightly upwardly as shown in FIG. 4. Web 44 will flex and permit ring 46 to lift off sealing ridge 35. Simultaneously, this will cause the tubular member 50 to move up within connector 30. This will create an outward flow path for exhaled air which can then flow up around the tubular member 50, over ridge 35, and out to atmosphere through openings 36.

If a malfunction occurs, and gas flow in pipe 12 is cut off, and the patient then attempts to inhale, a negative pressure is created within mask 14. In the absence of a slight positive pressure from the gas flow in chamber 16, the valve member 40 and particularly web 44 will then function as a diaphragm. Web 44 will flex and allow ring 46, and member 50 to rise upwardly into chamber 16, in an attempt to equalize the pressure throughout the system. Ring 46 will thus lift off ridge 35. At the same time, since the pressure within mask 14 is at this point slightly below atmospheric, air will flow inwardly through openings 36. Because ring 46 and member 50 have flexed inwardly into chamber 16, a slight spacing will open up around tubular member 50, permitting such outside air to flow inwardly, substantially in the same position as shown in FIG. 4, so that the patient can then continue to breathe normally.

If the patient should vomit into the mask, and if any vomit should pass over into the valve member 16, the mask can instantly be disconnected from the valve chamber, and the valve chamber can be removed from the gas supply pipe 12. The mask can then simply be washed or wiped clean. The valve chamber 16 can be opened up by a simple rotary unthreading action. The valve member 40 can be removed and washed. If when it is reassembled, the assistant attempts to assemble the valve member 40 the wrong way around, the skirt 42 will interfere so that the assistant will know that the valve member 40 is not in the correct position.

In the case of the treatment of infants it may be desirable to provide a pressure relief valve, to avoid overpressure. Such a relief valve is shown generally as 60 and has a body 62, and seat 64. A valve disc 66 is located on a rod 68. Spring 70 urges disc 66 onto seat 64. A threaded cap 72 retains spring 70 and permits adjustment of spring pressure. A finger button 74 permits holding of the disc 66 on seat 64 if it is desired to override the spring. Openings 76 in cap 72 permit release of gas during overpressure.

The foregoing is a description of a preferred embodiment of the invention which is given here by way of example only. The invention is not to be taken as limited to any of the specific features as described, but comprehends all such variations thereof as come withing the scope of the appended claims.

What is claimed is:

1. A breathing valve for use in association with breathing devices for the administration of gases to a patient, and comprising:

a valve chamber having an upstream end connectable to a supply of gas, and having a downstream end connectable to a breathing device, there being respective upstream and downstream openings in said chamber, whereby gas can be admitted through said upstream opening, and can be administered through said downstream opening in a first direction to said breathing device;

a tubular downstream connection member defining said downstream opening, and having upstream and downstream ends;

valve seating surfaces around said upstream end of said tubular connecting member;

gas flow passages in said chamber adjacent said upstream end of said tubular connection member whereby exhaled gases may pass from said breathing device through said tubular connection member in a second direction, and may be discharged to atmosphere, and through which atmospheric air may be inducted into said breathing device in a third direction;

a single integral flow control member extending across said chamber between said upstream and downstream ends, said flow control member in turn comprising:

a circular gas flow port located along the central axis of said flow control member;

one-way valve means incorporated in and forming an integral part of said flow control member in registration with said gas flow port whereby gas may flow from said chamber through said gas flow port and said valve means into said tubular connection member, said valve means preventing return flow in the oppositve direction through said valve means;

a thick, closure ring incorporated in and forming an integral part of said flow control member surrounding and defining said gas flow port and movable into and out of sealing engagement with said valve seating surfaces, whereby said closure ring will prevent communication between said tubular connection member and said gas flow passages upon inhalation of gas from said upstream end of said chamber;

said closure ring being movable away from said seating surfaces upon exhalation, thereby unsealing the same and allowing gas flow in said second direction through said tubular connection member and out of said gas flow passages;

peripheral mounting means formed integrally with said flow control member for securing the flow control member to said chamber; and, an annular pressure responsive thin, flexible diaphragm wall incorporated in and forming an integral part of said flow control member located between said peripheral mounting means and said thick closure ring and formed in section into a generally concave/convex annular fold with the convex profile directed towards said gas flow passages, and responsive to obstruction of gas flow into said chamber from said upstream end, and further responsive to inspiratory effort by a patient through said tubular connection member whereby to respond to the pressure difference created thereby and cause said closure ring to move away from said seating surfaces, thereby permitting inward air flow through said gas flow passages in said third direction into said tubular connection member for inhalation through said breathing device.

2. A breathing valve as claimed in claim 1 in which the flow control member has interference means to prevent assembly the wrong way around.

3. A breathing valve as claimed in claim 1 wherein such valve chamber is of two part construction, and including releasable fastening means for fastening the two parts of the valve chamber together, whereby it may readily be disassembled and reassembled for cleaning.

4. A breathing valve as claimed in claim 1 including an annular flange formed around said upstream end of such tubular member and extending outwardly therefrom, an opening in said valve chamber through which said tubular member passes, said opening being smaller than said flange, whereby said tubular member is retained in said chamber with a portion thereof extending outwardly through said opening, and retaining means on said tubular member outwardly of said chamber, preventing the same from being forced into said chamber, said tubular member being rotatable relative to said chamber in said opening to facilitate manipulation of the device in use in various positions.

5. A breathing valve as claimed in claim 4, wherein said gas flow passages are located adjacent said opening for receiving said tubular member.

6. A breathing valve as claimed in claim 1 wherein said valve means comprises an elongated tapering portion located inwardly of said closure ring, and extending therefrom into the end of said tubular member, said tapering portion defining two flexible lip portions, arranged so as to normally contact one another at their tips and being movable away from one another to permit one way flow of gas therethrough into said tubular member.

7. A breathing valve as claimed in claim 1 incorporating pressure relief valve means located in communication with said upstream end of said chamber, and, manual override means for overriding such pressure relief valve.

8. A breathing valve for use in association with breathing devices for the administration of gases to a patient, and comprising:

a valve chamber having an upstream and connectable to a supply of gas, and having a downstream end connectable to a breathing device, there being respective upstream and downstream openings in said chamber, whereby gas can be admitted through said upstream opening, and can be administered through said downstream opening in a first direction to said breathing device;

a tubular downstream connection member defining said downstream opening, and having upstream and downstream ends;

valve seating surfaces around said upstream end of said tubular connection member;

gas flow passages in said chamber adjacent said upstream end of said tubular connection member whereby exhaled gases may pass from said breathing device through said tubular connection member in a second direction, and may be discharged to atmosphere, and through which atmospheric air may be inducted into said breathing device in a third direction;

a single integral flow control member extending across said chamber between said upstream and downstream ends, said flow control member in turn comprising:

a circular gas flow port located along the central axis of said flow control member;

one-way valve means incorporated in and forming an integral part of said flow control member in registration with said gas flow port whereby gas may flow from said chamber through said gas flow port and said valve means into said tubular connection member, said valve means preventing return flow in the opposite direction through said valve means;

a thick closure ring incorporated in and forming an integral part of said flow control member surrounding and defining said gas flow port and movable into and out of sealing engagement with said valve seating surfaces, whereby said closure ring will prevent communication between said tubular connection member and said gas flow passages upon inhalation of gas from said upstream end of said chamber;

said closure ring being movable away from said seating surfaces upon exhalation, thereby unsealing the same and allowing gas flow in said second direction through said tubular connection member and out of said gas flow passages;

peripheral mounting means formed integrally with said flow control member for securing the flow control member to said chamber; and, an annular pressure responsive thin, flexible diaphragm wall incorporated in and forming an integral part of said flow control member located between said peripheral mounting means and said thick closure ring and formed in section into a generally concave annular fold, and responsive to obstruction of gas flow into said chamber from said upstream end, and further responsive to inspiratory effort by a patient through said tubular connection member whereby to respond to the pressure difference created thereby and cause said closure ring to move away from said seating surfaces, thereby permitting inward air flow through said gas flow passages in said third direction into said tubular connection member for inhalation through said breathing device; and, an annular flange formed around said upstream end of such tubular member and extending outwardly therefrom, an opening in said valve chamber through which said tubular member passes, said opening being smaller than said flange, whereby said tubular member is retained in said chamber with a portion thereof extending outwardly through said opening, and retaining means on said tubular member outwardly of said chamber, preventing the same from being forced into said chamber, said tubular member being rotatable relative to said chamber in said opening to facilitate manipulation of the device in use in various positions.

* * * * *